United States Patent
Conradie et al.

(10) Patent No.: US 10,273,518 B2
(45) Date of Patent: Apr. 30, 2019

(54) METHODS FOR BIOSYNTHESIZING 3-OXOPENT-4-ENOYL-COA

(71) Applicant: INVISTA NORTH AMERICA S.A.R.L., Wilmington, DE (US)

(72) Inventors: Alex Van Eck Conradie, Cleveland (GB); Adriana Leonora Botes, East Cleveland (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 119 days.

(21) Appl. No.: 14/908,659

(22) PCT Filed: Jul. 29, 2014

(86) PCT No.: PCT/US2014/048606
§ 371 (c)(1),
(2) Date: Jan. 29, 2016

(87) PCT Pub. No.: WO2015/017404
PCT Pub. Date: Feb. 5, 2015

(65) Prior Publication Data
US 2016/0168610 A1 Jun. 16, 2016

Related U.S. Application Data

(60) Provisional application No. 61/859,439, filed on Jul. 29, 2013.

(51) Int. Cl.
*C12P 19/32* (2006.01)
*C12P 7/40* (2006.01)
*C12P 7/26* (2006.01)
*C12N 9/10* (2006.01)

(52) U.S. Cl.
CPC .......... *C12P 19/32* (2013.01); *C12N 9/1029* (2013.01); *C12P 7/26* (2013.01); *C12P 7/40* (2013.01); *C12Y 203/01016* (2013.01)

(58) Field of Classification Search
CPC . C12N 9/1029; C12Y 203/01016; C12P 7/26; C12P 7/40; C12P 19/32
See application file for complete search history.

(56) References Cited

U.S. PATENT DOCUMENTS

2012/0021478 A1  1/2012  Osterhout et al.
2013/0122563 A1*  5/2013  Burk .................... C12P 5/026
                                                          435/167

FOREIGN PATENT DOCUMENTS

WO    2013/082542 A2    6/2013
WO    2015/017404 A1    2/2015

OTHER PUBLICATIONS

Branden et al., Introduction to Protein Structure, Garland Publishing Inc., New York, p. 247.*
Seffernick et al., J. Bacteriol. 183(8):2405-2410, 2001.*
Witkowski et al., Biochemistry 38:11643-11650, 1999.*
Sadowski et al., Current Opinion in Structural Biology 19:357-362, 2009.*
Feng et al., GenBank accession No. AEB40065, Jun. 1, 2011.*
International Search Report and Written Opinion received for PCT Patent Application No. PCT/US2014/048606, dated Oct. 31, 2014, 10 pages.
International Preliminary Report on Patentability received for PCT Patent Application No. PCT/US2014/048606, dated Feb. 11, 2016, 7 pages.
Becker et al., "Metabolic Flux Engineering of l-lysine Production in Corynebacterium Glutamicum—Over Expression and Modification of G6P Dehydrogenase", Journal of Biotechnology, vol. 132, Issue 2, Oct. 31, 2007, pp. 99-109.
Brigham et al., "Engineering Ralstonia Eutropha for Production of Isobutanol from CO2, H2, and O2", Advanced Biofuels and Bioproducts, Chapter 39, Jan. 2013, pp. 1065-1090.
Bugg et al., "The Emerging Role for Bacteria in Lignin Degradation and Bio-product Formation", Current Opinion in Biotechnology, vol. 22, Issue 3, Jun. 2011, pp. 394-400.
Hermann, Thomas, "Industrial Production of Amino Acids by Coryneform Bacteria", Journal of Biotechnology, vol. 104, Issues 1-3, Sep. 4, 2003, pp. 155-172.
Park et al., "Generic *Escherichia coli* Contamination of Spinach at the Preharves Stage: Effects of Farm Management and Environmental Factors", Applied and Environmental Microbiology, vol. 79, Issue 14, 2013, pp. 4347-4358.
Jang et al., "Bio-based Production of C2—C6 Platform Chemicals", Biotechnology & Bioengineering, vol. 109, No. 10, Oct. 2012, pp. 2437-2459.
Jaremko et al., "The Initial Metabolic Conversion of Levulinic Acid in Cupriavidus Necator", Journal of Biotechnology, vol. 155, Issue 3, Sep. 20, 2011, pp. 293-298.
Kanehisa et al., "Kegg: Kyoto Encyclopedia of Genes and Genomes", Nucleic Acids Research, vol. 28, No. 1, 2000, pp. 27-30.
Kanehisa et al., "Kegg for Integration and Interpretation of Large-scale Molecular Data Sets", Nucleic Acids Research, vol. 40, 2012, pp. D109-D114.
Köpke et al., "2,3-Butanediol Production by Acetogenic Bacteria, an Alternative Route to Chemical Synthesis, Using Industrial Waste Gas", Applied and Environmental Microbiology, vol. 77, No. 15, Aug. 2011, pp. 5467-5475.
Lee et al., "Synthesis of Pure meso-2,3-Butanediol from Crude Glycerol Using an Engineered Metabolic Pathway in *Escherichia coli*", Applied Biochemistry and Biotechnology, vol. 166, Issue 7, Apr. 2012, pp. 1801-1813.
Li et al. "Cupriavidus Necator JMP134 Rapidly Reduces Furfural with a Zn-Dependent Alcohol Dehydrogenase", Biodegradation, vol. 22, Apr. 28, 2011, pp. 1215-1225.
Lim et al., "Amplification of the NADPH-Related Genes zwf and gnd for the Oddball Biosynthesis of PHB in an *E. coli* Transformant Harboring a Cloned phbCAB Operon", Journal of Bioscience and Bioengineering, vol. 93, Issue 6, 2002, pp. 543-549.

(Continued)

*Primary Examiner* — Delia M Ramirez
(74) *Attorney, Agent, or Firm* — Licata & Tyrrell P.C.

(57) ABSTRACT

This document describes biochemical pathways that include the production of 3-oxopent-4-enoyl-CoA by condensation of acryloyl-CoA and acetyl-CoA using a β-ketothiolase with a SER-HIS-HIS catalytic triad. These pathways described herein rely on enzymes such as, inter alia, dehydrogenases, dehydratases and β-ketothiolases.

15 Claims, 6 Drawing Sheets
Specification includes a Sequence Listing.

(56) References Cited

OTHER PUBLICATIONS

Martin, et al., "High-titer Production of Monomeric Hydroxyvalerates From Levulinic Acid in Pseudomonas putida", Journal of Biotechnology, vol. 139, Issue 1, Jan. 1, 2009, pp. 61-67.

Meijnen et al., "Improved p-hydroxyBenzoate Production by Engineered Pseudomonas putida S12 by Using a Mixed-substrate Feeding Strategy", Applied Microbiology and Biotechnology, vol. 90, Feb. 2, 2011, pp. 885-893.

Modis et al., "A Biosynthetic Thiolase in Complex With a Reaction Intermediate: The Crystal Structure Provides New Insights Into the Catalytic Mechanism", Structure, vol. 7, Issue 10, 1999, pp. 1279-1290.

Ohashi et al., "Continuous Production of Lactic Acid from Molasses by Perfusion Culture of Lactococcus Lactis Using a Stirred Ceramic Membrane Reactor", Journal of Bioscience and Bioengineering, vol. 87, Issue 5, 1999, pp. 647-654.

Palmer et al., "Biosynthetic Thiolase from Zoogloea Ramigera: Evidence for a Mechanism Involving Cys-378 as the Active Site Base", The Journal of Biological Chemistry, vol. 266, No. 13, 1991, pp. 8369-8375.

Papanikolaou et al., "Citric Acid Production by Yarrowia Lipolytica Cultivated on Olive-Mill Wastewater-Based Media", Bioresource Technology, vol. 99, Issue 7, May 7, 2008, pp. 2419-2428.

Perez-Pantoja, et al., "Metabolic Reconstruction of Aromatic Compounds Degradation from the Genome of the Amazing Pollutant-Degrading Bacterium Cupriavidus Necator JMP134", FEMS Microbiology Reviews, vol. 32, Aug. 7, 2008, pp. 736-794.

Prybylski et al., "Third-Generation Feed Stocks for the Clean and Sustainable Biotechnological Production of Bulk Chemicals: Synthesis of 2-Hydroxyisobutyric Acid", Energy, Sustainability and Society, vol. 2, No. 11, Jul. 16, 2012, 9 pages.

Ramsay et al., "Use of a Nylon Manufacturing Waste as an Industrial Fermentation Substrate", Applied and Environmental Microbiology, vol. 52, No. 1, Jul. 1986, pp. 152-156.

Seedorf et al., "The Genome of Clostridium Kluyveri, A Strict Anaerobe with Unique Metabolic Features", PNAS USA, vol. 105, No. 6, Feb. 12, 2008, pp. 2128-2133.

Shen et al., "Driving Forces Enable High-Titer Anaerobic 1-Butanol Synthesis in *Escherichia coli*", Applied and Environmental Microbiology, vol. 77, No. 9, May 2011, pp. 2905-2915.

Tseng et al., "Biosynthesis of Chiral 3-Hydroxyvalerate from Single Propionate-Unrelated Carbon Sources in Metabolically Engineered *E. coli*", Microbial Cell Factories, vol. 9, No. 96, Nov. 27, 2010, 12 pages.

Upton, et al., "Role of the methylcitrate Cycle in Propionate Metabolism and Detoxification in *Mycobacterium smegmatis*", Microbiology, vol. 153, Dec. 2007, pp. 3973-3982.

Wee et al., "Biotechnological Production of Lactic Acid and Its Recent Applications", Food Technology and Biotechnology, vol. 44, No. 2, 2006, pp. 163-172.

White, Claude WM., "Butadiene Production Process Overview", Chemico-Biological Interactions, vol. 166, Issues 1-3, Mar. 20, 2007, pp. 10-14.

Yang et al., "Value-added Uses for Crude Glycerol—a Byproduct of Biodiesel Production", Biotechnology for Biofuels, vol. 5, No. 13, Mar. 14, 2012, 10 pages.

UniPortKB-I3RA72, "3-ketoacyl-CoA thiolase", bktBa, UniPort, Sep. 5, 2012, 6 pages.

\* cited by examiner

```
          10         20         30         40         50         60
MEVAVIGSSM TKFGQRSAWI RELLSEAGQA CLEDAGVAPA SVDHLIVSNM ASGEFEGQTG 70         80         90        100        110        120
VMNALAHDLG VIPAYTQRID QTSSSGGAGI YEAWQSIASG VSEMTLLVGG EKMTHKTTGE 130        140        150        160        170        180
STDIIASCTH PEEYKHGVTL PSFAGMTARN YLERFDAPRE SLARVAVKNH RNGVDNPKAQ 190        200        210        220        230        240
FQKEIDIETA LESPIIADPL RLYDECPITD GSAAMFTTE ERAQEITDEY AIVSGVGGAT 250        260        270        280        290        300
DTHVVHERDD PTVMGGVVES SKQAYEMAGV GPDDLDVAEL HDMFTLLEFL QLEGIGVADH 310        320        330        340        350        360
GAAWELAMDG VTAKDGGLPI NTSGGLKSKG HPLGASGVAQ GVEIYEQLVG EAGPRQVEAD 370        380
TALACNVGGF GNCVITTIME AAK
```

FIGURE 6

```
         10         20         30         40         50         60
MAIVEFEVDG QAVRALGQVT TDDIETGDVV EPVYVEELRD PEVGIKAPES QSWDGYRWDP V
```

METHODS FOR BIOSYNTHESIZING 3-OXOPENT-4-ENOYL-COA

CROSS-REFERENCE TO PRIOR APPLICATION

This application is a U.S. National Stage Application of PCT/US2014/048606 filed Jul. 29, 2014 and claims priority from U.S. Provisional Patent Application Ser. No. 61/859,439 filed Jul. 29, 2013, the entire contents of each of which are incorporated herein by reference in their entirety.

TECHNICAL FIELD

This invention relates to methods for biosynthesizing 3-oxopent-4-enoyl-CoA, and more particularly to synthesizing 3-oxopent-4-enoyl-CoA as a bio-based precursor to 1,3-butadiene, using one or more isolated enzymes such as dehydrogenases, dehydratases and β-ketothiolases, or using recombinant host cells expressing one or more of such enzymes.

BACKGROUND 1,3-Butadiene (sometimes referred to herein as "butadiene") is an important monomer for the production of synthetic rubbers including styrene-butadiene-rubber (SBR), polybutadiene (PB), styrene-butadiene latex (SBL), acrylonitrile-butadiene-styrene resins (ABS), nitrile rubber, and adiponitrile. Adiponitrile is used in the manufacture of Nylon-66 (White, Chemico-Biological Interactions, 2007, 166, 10-14).

Butadiene is typically produced as a co-product from the steam cracking process, distilled to a crude butadiene stream, and purified via extractive distillation (White, Chemico-Biological Interactions, 2007, 166, 10-14).

On-purpose butadiene has been prepared among other methods by dehydrogenation of n-butane and n-butene (Houdry process); and oxidative dehydrogenation of n-butene (Oxo-D or O-X-D process) (White, Chemico-Biological Interactions, 2007, 166, 10-14).

Industrially, 95% of global butadiene production is undertaken via the steam cracking process using petrochemical-based feedstocks such as naphtha. Production of on-purpose butadiene is not significant, given the high cost of production and low process yield (White, Chemico-Biological Interactions, 2007, 166, 10-14).

Given reliance on petrochemical feedstocks and, for on-purpose butadiene, energy intensive catalytic steps; biotechnology offers an alternative approach via biocatalysis. Biocatalysis is the use of biological catalysts, such as enzymes, to perform biochemical transformations of organic compounds.

Accordingly, against this background, it is clear that there is a need for sustainable methods for producing intermediates, in particular butadiene, wherein the methods are biocatalyst based (Jang et al., Biotechnology & Bioengineering, 2012, 109(10), 2437-2459).

Both bioderived feedstocks and petrochemical feedstocks are viable starting materials for the biocatalysis processes.

There are no known enzyme pathways leading to the synthesis of butadiene in prokaryotes or eukaryotes. Three potential pathways have been suggested for producing 1,3-butadiene from biomass-sugar: (1) from acetyl-CoA via crotonyl-CoA; (2) from erythrose-4-phosphate; and (3) via a condensation reaction with malonyl-CoA and acetyl-CoA. However, no performance information using these strategies has been reported (Jang et al., Biotechnology & Bioengineering, 2012, 109(10), 2437-2459).

An alternate pathway strategy using 3-oxopent-4-enoyl-CoA as a precursor to 1,3-butadiene is a plausible route to the synthesis of 1,3-butadiene via biocatalysis processes (See WO2013082542 A2).

SUMMARY

Synthesis of 3-oxopent-4-enoyl-CoA via β-ketothiolase activity, such as the gene product of bktB classified under EC 2.3.1.16, would entail condensation of acryloyl-CoA and acetyl-CoA. However, acryloyl-CoA is an inactivator of β-ketothiolases reliant on a CYS-HIS-CYS catalytic triad, as is typical for polyhydroxybutyrate producing bacterial species (Palmer et al., Journal of Biological Chemistry, 1991, 266(13), 8369-8375; Modis & Wierenga, Structure, 1999, 7, 1279-1290).

This document is based at least in part on the conclusion by the inventors that the SER-HIS-HIS catalytic triad associated with β-ketothiolase activity from haloarchaea (Hou et al., Appl. Environ. Microbiol., 2013, 79(14)), as opposed to the CYS-HIS-CYS catalytic triad of other β-ketothiolases, would not be inactivated by acryloyl-CoA and that it is possible to construct biochemical pathways producing 3-oxopent-4-enoyl-CoA as a precursor leading to the synthesis of butadiene. These pathways that are described herein rely on enzymes such as dehydrogenases, dehydratases and β-ketothiolases.

Enzymes capable of condensing acryloyl-CoA and acetyl-CoA have not previously been described or suggested.

Figure 4:
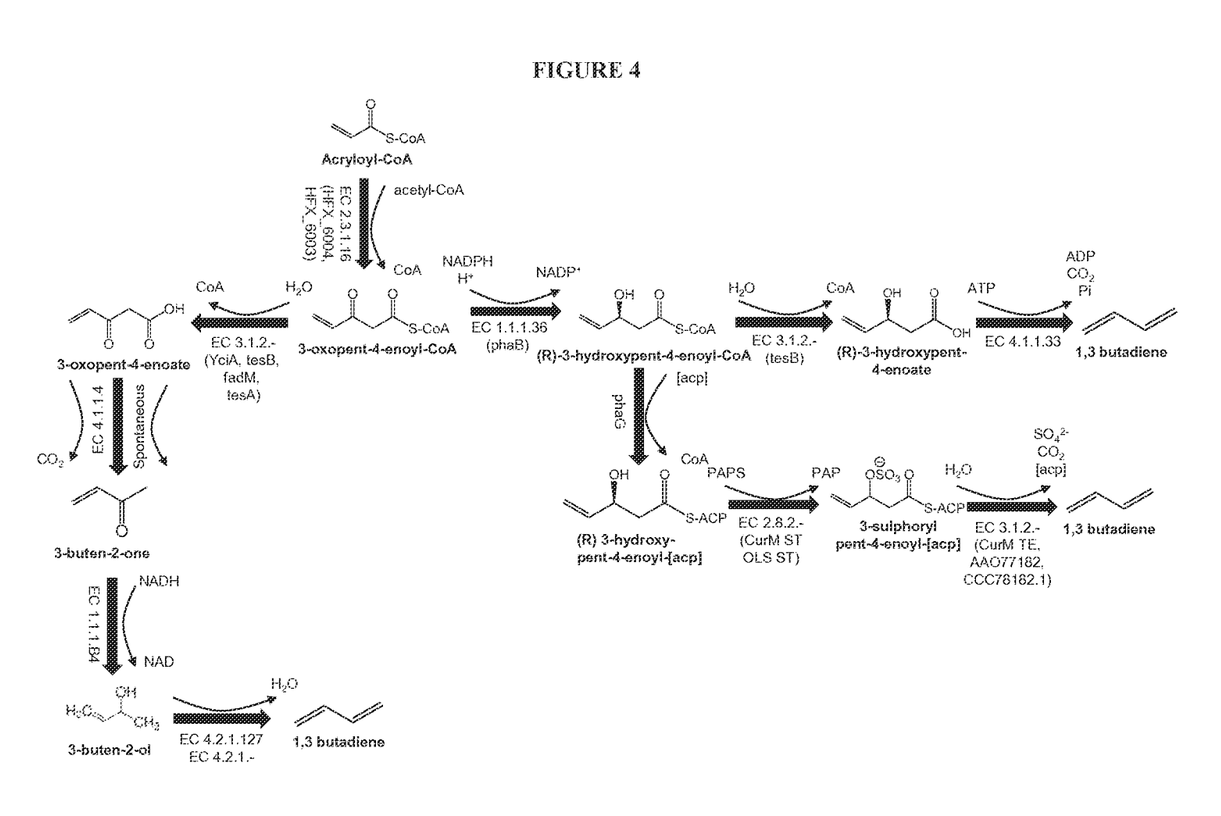
FIG. 4 is a schematic of biochemical pathways leading to the production of 1,3-butadiene using 3-oxopent-4-enoyl-CoA as central precursor.

Thus, in one aspect, this document provides enzymes that can produce 3-oxopent-4-enoyl-CoA, serving as a precursor in the synthesis of butadiene (See FIG. 4).

In some embodiments, the condensation of acryloyl-CoA and acetyl-CoA to form 3-oxopent-4-enoyl-CoA is catalysed via β-ketothiolase activity not reliant on cysteine residues for catalysis such as the CYS-HIS-CYS catalytic triad associated with particularly polyhydroxybutyrate producing bacterial species.

In some embodiments, the condensation of acryloyl-CoA and acetyl-CoA to form 3-oxopent-4-enoyl-CoA is catalysed via β-ketothiolase activity, such as encoded by HFX_6004 (bktBα) and HFX_6003 (bktBβ), associated with haloarchaea. The gene product of the bktBα endows the β-ketothiolase with its substrate specificity.

In some embodiments, the condensation of acryloyl-CoA and acetyl-CoA to form 3-oxopent-4-enoyl-CoA is catalysed via β-ketothiolase activity associated with a SER-HIS-HIS catalytic triad.

Figure 2:
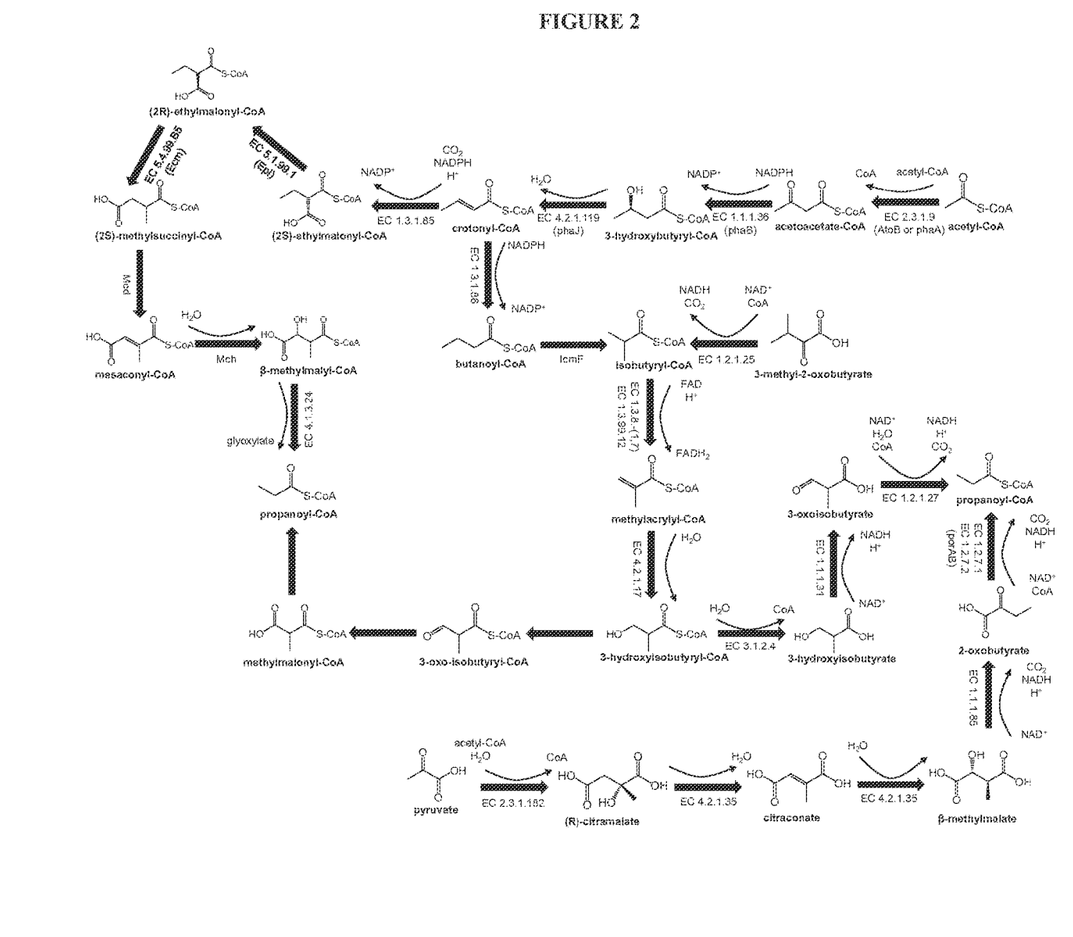
FIG. 2 is a schematic of biochemical pathways leading to the production of propanoyl-CoA from central metabolites.
Figure 3:
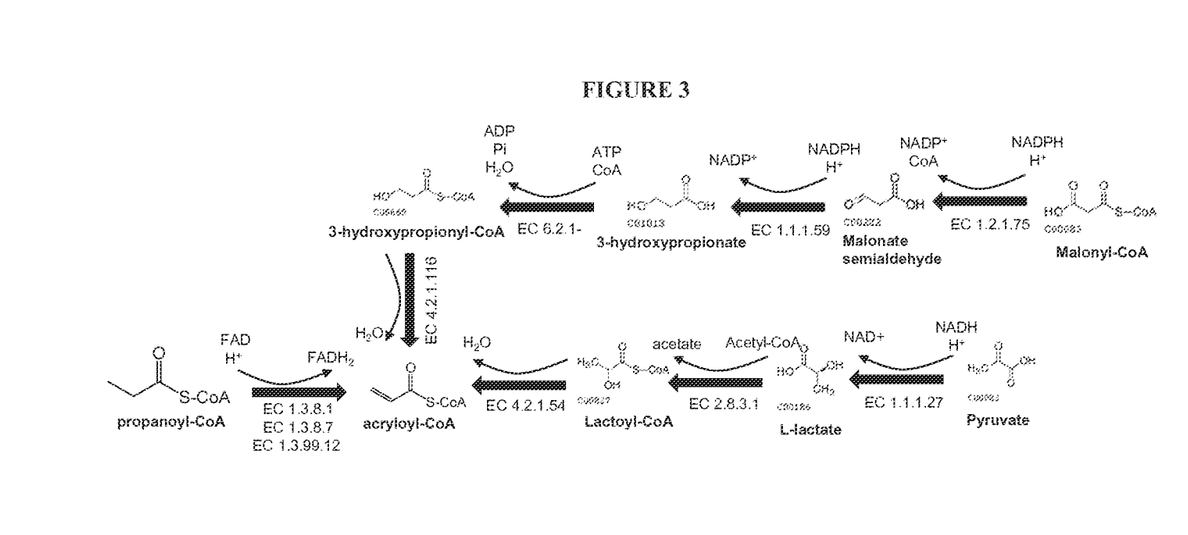
FIG. 3 is a schematic of biochemical pathways leading to the production of acryloyl-CoA.

In some embodiments, acryloyl-CoA can be produced from propanoyl-CoA by using a short-chain acyl-CoA dehydrogenase such as classified under EC 1.3.8.1 or EC 1.3.8.7 or a 2-methylacyl-CoA dehydrogenase such as classified under EC 1.3.99.12 (See FIG. 3). Propanoyl-CoA can be produced via numerous pathways as described in FIG. 1 and FIG. 2.

In some embodiments, acryloyl-CoA can be produced from 3-hydroxypropionoyl-CoA using a 3-hydroxypropionyl-CoA dehydratase such as classified under EC 4.2.1.116 (See FIG. 2). The 3-hydroxypropionyl-CoA can be produced from 3-hydroxypropionate using a CoA-ligase such as classified under EC 6.2.1.-. The 3-hydroxypropionate can be produced from malonate semialdehyde using a 3-hydroxypropionate dehydrogenase such as classified under EC 1.1.1.59 (See FIG. 3). The malonate semialdehyde can be produced from the central metabolite malonyl-CoA using a malonyl-CoA reductase such as classified under EC 1.2.1.75.

In some embodiments, acryloyl-CoA can be produced from lactoyl-CoA using a lactoyl-CoA dehydratase such as classified under EC 4.2.1.54 (See FIG. 3). The lactoyl-CoA can be produced from lactate using a propionate CoA-transferase such as classified under EC 2.8.3.1. The lactate can be produced from pyruvate using a lactate dehydrogenase such as classified under EC 1.1.1.27.

In any of the methods described herein, the method can be performed using isolated enzymes, using cell lysates comprising the enzymes, or using a recombinant host.

The recombinant host can be anaerobically, micro-aerobically or aerobically cultivated.

Recombinant host cells can be retained in ceramic hollow fiber membranes to maintain a high cell density during fermentation.

The principal carbon source fed to the fermentation can derive from biological or non-biological feedstocks. For example, the biological feedstock can be, or can be derived from, monosaccharides, disaccharides, lignocellulose, hemicellulose, cellulose, levulinic acid, furfural, lignin, triglycerides such as glycerol and fatty acids, agricultural waste or municipal waste. The non-biological feedstock can be, or can be derived from, either natural gas, syngas, $CO_2/H_2$, methanol, ethanol, non-volatile residue (NVR) or caustic wash waste stream from cyclohexane oxidation processes.

The host microorganism can be a prokaryote from the genus *Escherichia* such as *Escherichia coli*; from the genus *Clostridia* such as *Clostridium ljungdahlii, Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*.

The host microorganism can be a eukaryote from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*.

In any of the recombinant hosts described herein, the enzymes catalyzing the hydrolysis of propionyl-CoA and acetyl-CoA can be attenuated; the enzymes consuming propanoyl-CoA via the methyl-citrate cycle can be attenuated; the enzymes consuming propanoyl-CoA to pyruvate can be attenuated; the enzymes consuming propanoyl-CoA to malonyl-CoA can be attenuated; a feedback-resistant threonine deaminase can be genetically engineered into the host organism; the β-ketothiolases catalyzing the condensation of acetyl-CoA to acetoacetyl-CoA such as the gene products of AtoB or phaA can be attenuated; the polymer synthase enzymes in a host strain that naturally accumulates polyhydroxyalkanoates can be attenuated; a gene encoding a phosphotransacetylase, such as pta, can be attenuated; a gene encoding an acetate kinase degrading propanoate, such as ack, can be attenuated; a gene encoding the degradation of pyruvate to lactate can be attenuated; a gene encoding the degradation of phophoenolpyruvate to succinate such as frdBC can be attenuated; a gene encoding the degradation of acetyl-CoA to ethanol such as adhE can be attenuated; the enzymes catalyzing anaplerotic reactions supplementing the citric acid cycle intermediates can be amplified; a puridine nucleotide transhydrogenase gene such as UdhA can be overexpressed; a glyceraldehyde-3P-dehydrogenase gene such as GapN can be overexpressed in the host organisms; a malic enzyme gene such as maeA or maeB can be overexpressed in the host organism; a glucose-6-phosphate dehydrogenase gene such as zwf can be overexpressed in the host organism; a fructose 1,6 diphosphatase gene such as fbp can be overexpressed in the host organism.

More specifically, the present document provides a method of 3-oxopent-4-enoyl-CoA synthesis; the method can include the condensation of acryloyl-CoA and acetyl-CoA using a protein with β-ketothiolase activity. At least one subunit of the protein can be a polypeptide, or can be derived from a polypeptide, encoded by an archaeon gene, e.g., a haloarchaeon gene. The protein can contain a SER-HIS-HIS catalytic triad associated with its catalytic mechanism.

In addition, the protein can be a heterodimer in which one or both of the two polypeptides of the heterodimer are: full-length gene products of the *Haloferax mediterranei* HFX_6004 (bktBα) and HFX_6003 (bktBβ) genes; biologically active fragments of the gene products; or biologically active variants of the full-length gene products or the biologically active fragments. One or both of the polypeptides can be an engineered polypeptide having greater than 50% homology to the corresponding polypeptide chain of the BktB β-ketothiolase of *Haloferax mediterranei*.

In any of the methods, the acryloyl-CoA can be produced using a butyryl-CoA dehydrogenase (EC 1.3.8.1), a medium-chain acyl-CoA dehydrogenase (EC 1.3.8.7), a 2-methylacyl-CoA dehydrogenase (EC 1.3.99.12), a lactoyl-CoA dehydratase (EC 4.2.1.54), or a 3-hydroxypropionyl-CoA dehydratase (EC 4.2.1.116).

Any of the above methods can include a fermentation process using a host cell expressing the protein. The host cell can be a prokaryote or a eukaryote. The prokaryote can be a bacterium of the genus *Escherichia* such as *Escherichia coli*; of the genus *Clostridia* such as *Clostridium ljungdahlii, Clostridium autoethanogenum* or *Clostridium kluyveri*; of the genus *Corynebacteria* such as *Corynebacterium glutamicum*; of the genus *Cupriavidus* such as *Cupriavidus necator* or *Cupriavidus metallidurans*; of the genus *Pseudomonas* such as *Pseudomonas fluorescens* or *Pseudomonas putida*; of the genus *Bacillus* such as *Bacillus subtillis*; or of the genus *Rhodococcus* such as *Rhodococcus equi*. Alternatively, the prokaryote can be an archaeon of the genus *Methanocaldococcus* such as *Methanocalcococcus jannaschii*; of the genus *Haloferax* such as *Haloferax mediterranei*; of the genus *Metallosphera* such as *Metallosphera sedula*; of the genus *Methanobacterium* such as *Methanobacterium thermoautotrophicum*; or of the genus *Pyrococcus* such as *Pyrococcus abyssi*. The eukaryote can be a fungus of the genus *Aspergillus* such as *Aspergillus niger*; of the genus *Saccharomyces* such as *Saccharomyces cerevisiae*; of the genus *Pichia* such as *Pichia pastoris*; of the genus *Yarrowia* such as *Yarrowia lipolytica*; of the genus *Issatchenkia* such as *Issathenkia orientalis*; of the genus *Debaryomyces* such as *Debaryomyces hansenii*; of the genus *Arxula* such as *Arxula adenoinivorans*; or of the genus *Kluyveromyces* such as *Kluyveromyces lactis*. The fermentation process of any of the above methods can include anaerobic, micro-aerobic or aerobic cell cultivation. Moreover, cell retention strategies using, for example, ceramic hollow fiber membranes can be employed to achieve and maintain a high cell density during fermentation. Furthermore, the principal carbon source fed to the fermentation can derive from biological or non-biological feedstocks. The biological feedstock can be, or can be derived from, monosaccharides, disaccharides, hemicellulose such as levulinic acid and furfural, cellulose, lignocellulose, lignin, triglycerides such as glycerol and fatty acids, agricultural waste or municipal waste. In addition, the non-biological feedstock can be, or can be derived from, natural gas, syngas, $CO_2/H_2$, methanol, ethanol, non-volatile residue (NVR), caustic wash from a cyclohexane oxidation processes, or other waste stream from the chemical or petrochemical industries.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF DRAWINGS

Images with KEGG Entry ID numbers in FIG. 1 to FIG. 4 originate from the world wide web at genome.jp/kegg (Kanehisa and Goto, *Nucleic Acids Res.*, 2012, 40, D109-D114; Kanehisa and Goto, *Nucleic Acids Res.*, 2000, 28, 27-30).

DETAILED DESCRIPTION

In particular, this document provides enzymes, non-natural pathways, cultivation strategies, feedstocks, host microorganisms and attenuations to the host's biochemical network, which allow the production of 3-oxopent-4-enoyl-CoA as central precursor leading to the synthesis of 1,3 butadiene (sometimes referred to as "butadiene" herein) from central metabolites. As used herein, the term "central precursor" is used to denote any metabolite in any metabolic pathway shown herein leading to the synthesis of 3-oxopent-4-enoyl-CoA and/or butadiene. The term "central metabolite" is used herein to denote a metabolite that is produced in all microorganisms to support growth.

Figure 5:
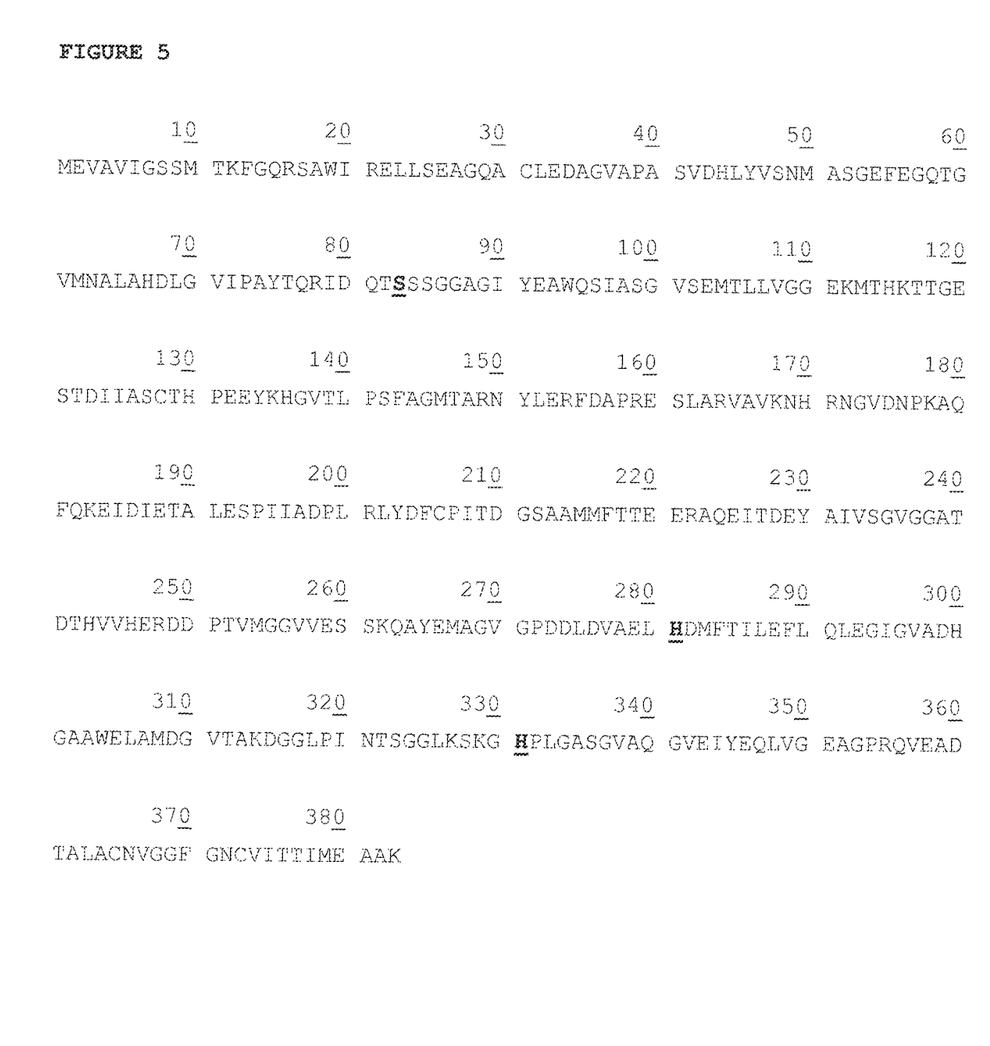
FIG. 5 is a depiction of the amino acid sequence of the *Haloferax mediterranei* β-ketothiolase α-chain (BktBα) (Genbank Accession No. AFK21132.1, SEQ ID NO: 1). The amino acids of the SER-HIS-HIS catalytic triad are shown in bold and underlined.
Figure 6:
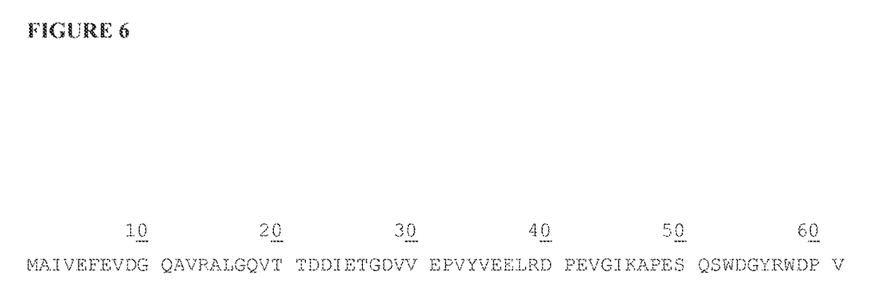
FIG. 6 is a depiction of the amino acid sequence of the *Haloferax mediterranei* β-ketothiolase β-chain (BktBβ) (Genbank accession No. AFK21131.1, SEQ ID NO: 2).

As such, host microorganisms described herein can include endogenous pathways that can be manipulated such that 3-oxopent-4-enoyl-CoA can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host. Within an engineered pathway, the enzymes can be from a single source, i.e., from one species, or can be from multiple sources, i.e., different species. Nucleic acids encoding the enzymes described herein have been identified from various organisms and are readily available in publicly available databases such as GenBank or EMBL.

Where the enzyme is one having the β-ketothiolase activity described herein, the enzyme will most commonly be one that is, or is derived from an archaeon, e.g., the haloarchaeon *Haloferax mediterranei*. The active form of this enzyme is a heterodimer composed of an α-chain and β-chain, referred to as BktBα and BktBβ, respectively. The genes encoding these two polypeptides in *H. mediterranei* are referred to as HFX_6004 (or bktBα) and HFX_6003 (or bktBβ), respectively. Contrary to other β-ketothiolases, which are homotetramers and contain a CYS-HIS-CYS catalytic triad, the *H. mediterranei* enzyme contains a SER-HIS-HIS catalytic triad (Hou et al., *Appl. Environ. Microbiol.*, 2013, 79(14)). It is noted that the amino acids of neither the CYS-HIS-CYS nor the SER-HIS-HIS catalytic triads are consecutively located on the relevant polypeptide subunit but are separated by different numbers of amino acids. FIG. 5 shows the amino acid sequence of the *H. mediterranei* BktBα subunit (SEQ ID NO: 1) containing the SER-HIS-HIS triad and the relevant SER and HIS residues of the catalytic triad are shown in bold and underlined; the three residues are located at amino acid positions 83, 281, and 331, respectively. The catalytic function of the three amino acids was predicted by bioinformatics analyses (amino acid sequence alignments (BLAST (see below for more details) and the GenDoc programs) and prediction by the NCBI conserved domain search (CDD) service) and confirmed by genetic and functional studies (Hou et al., *Appl. Environ. Microbiol.*, 2013, 79(14)). While the BktBα subunit endows the substrate specificity of the enzyme, the BktBβ subunit (amino acid sequence of the *H. mediterranei* BktBβ subunit shown in FIG. 6, SEQ ID NO:2) appears also to be essential for its activity and it seems that an OB fold (oligonucleotide/oligosaccharide-binding fold) in the BktBβ subunit (at amino acid residues 32-94 in the *H. mediterranei* BktBβ subunit) is required for the activity (Hou et al., *Appl. Environ. Microbiol.*, 2013, 79(14)). Bioinformatic analyses (such as those mentioned above) together with genetic and functional studies well known in the art can be used to identify the amino acid residues and regions of the SER-HIS-HIS catalytic triad (e.g., the region corresponding to amino acids 83-331 of the *H. mediterranei* BktBα subunit) and the OB fold (e.g., the region corresponding to as amino acids 32-94 of the *H. mediterranei* BktBβ subunit) in the other β-ketothiolase polypeptides.

Functional fragments of any of the enzymes, or enzyme subunits, described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity. It will be understood that, in the case of BktBα chains, such fragments should preferably be, or contain, the region containing the SER-HIS-HIS catalytic triad (such as amino acids 83-331 of the *H. mediterranei* BktBα chain). Moreover, in the case of BktBβ chains, such fragments should preferably be, or contain, the region containing the OB fold (such as amino acids 32-94 of the *H. mediterranei* BktBβ subunit).

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagluttanin (HA), glutathione-S-transferase (GST), or maltose binding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

All the enzymes, or enzyme subunits, described herein that can be used for 3-oxopent-4-enoyl-CoA and/or butadiene production can have at least 50% sequence identity (homology) (e.g., at least 55%, 60%, 65%, 70%, 75%, 80%, 85%, 90%, 95%, 97%, 98%, 99%, or 100%) to the amino acid sequence of the corresponding wild-type enzyme or enzyme subunit. The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., fr. with the extension com/blast/ of the world wide web) or the U.S. government's National Center for Biotechnology Information web site (ncbi. with the extension nlm.nih.gov of the world wide web). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt j c:\seq2.txt p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be used for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It is understood that substitutions and deletions will not be of the three amino acids of the SER-HIS-HIS catalytic triad of the BtkBα subunit. Moreover, substitutions, deletions, and additions will preferably be outside the region of the BtkBα chain containing the catalytic triad (see above) and outside the region of BtkBβ subunit polypeptide containing the OB fold (see above).

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Engineered hosts can naturally express none or some (e.g., one or more, two or more, three or more, four or more, five or more, or six or more) of the enzymes of the pathways described herein. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. Thus, as described herein recombinant hosts can include nucleic acids encoding one or more of a dehydrogenase, a dehydratase or a β-ketothiolase as described in more detail below.

In addition, the production of 3-oxopent-4-enoyl-CoA can be performed in vitro using the isolated enzymes described herein, using a lysate (e.g., a cell lysate) from a host microorganism as a source of the enzymes, or using a plurality of lysates from different host microorganisms as the source of the enzymes.

Enzymes and Pathways Generating acryloyl-CoA (e.g., to be Used for the Biosynthesis of 3-oxopent-4-enoyl-CoA)

As depicted in FIG. 3, acryloyl-CoA can be produced from 3 hydroxypropionyl-CoA, propanoyl-CoA or lactoyl-CoA.

In some embodiments, acryloyl-CoA can be produced from: (a) propanoyl-CoA by a butyryl-CoA dehydrogenase (EC 1.3.8.1), a medium-chain acyl-CoA dehydrogenase (EC 1.3.8.7), or a 2-methylacyl-CoA dehydrogenase (EC 1.3.99.12); (b) lactoyl-CoA by a lactoyl-CoA dehydratase (EC 4.2.1.54); or (c) 3-hydroxypropionyl-CoA by a 3-hydroxypropionyl-CoA dehydratase (EC 4.2.1.116) (See, FIG. 3).

Figure 1:
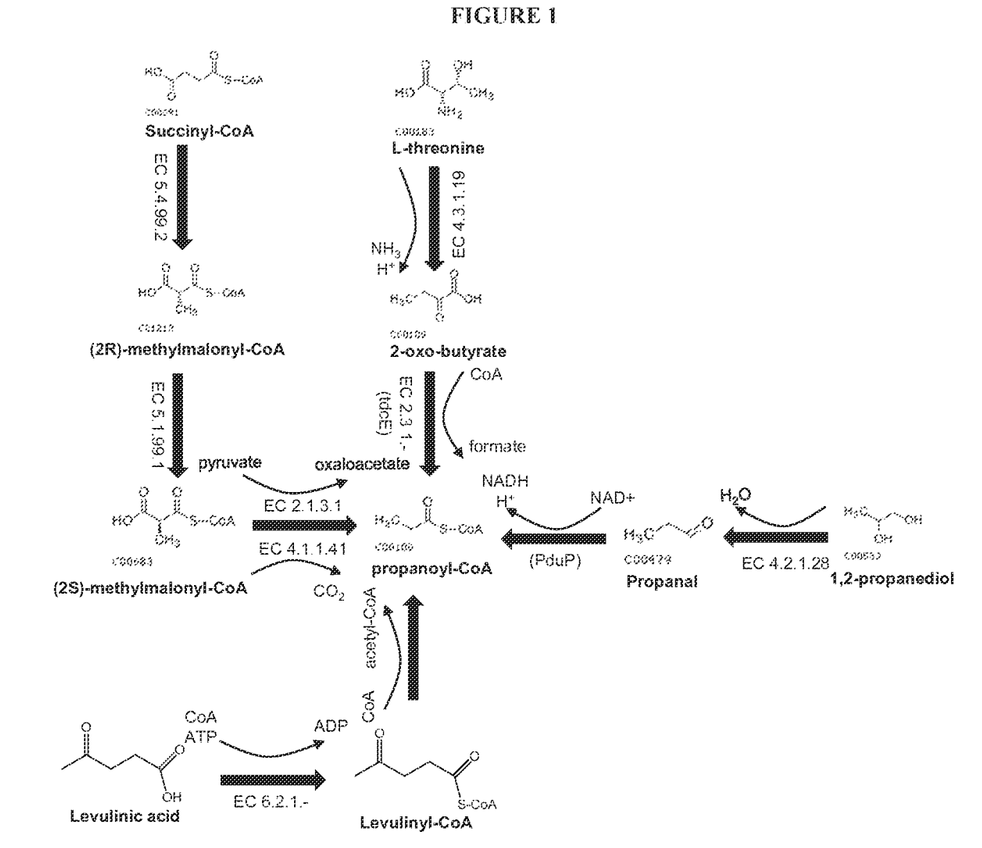
FIG. 1 is a schematic of biochemical pathways leading to the production of propanoyl-CoA from central metabolites.

Propanoyl-CoA can be produced via several pathways as described in FIG. 1 and FIG. 2.

In some embodiments, 3-hydroxypropionyl-CoA can be produced from 3-hydroxypropionate using a CoA-ligase such as that classified under EC 6.2.1.- (FIG. 3). The 3-hydroxypropionate can be produced from malonate semialdehyde using a 3-hydroxypropionate dehydrogenase such as that classified under EC 1.1.1.59 (FIG. 3). The malonate semialdehyde can be produced from the central metabolite malonyl-CoA using a malonyl-CoA reductase such as that classified under EC 1.2.1.75 (FIG. 3).

In some embodiments, lactoyl-CoA can be produced from lactate using a propionate CoA-transferase such as classified under EC 2.8.3.1 (FIG. 3). The lactate can be produced from pyruvate using a lactate dehydrogenase such as classified under EC 1.1.1.27 (FIG. 3).

Enzymes Generating the 3-oxopent-4-enoyl-CoA

In some embodiments, the condensation of acryloyl-CoA and acetyl-CoA to form 3-oxopent-4-enoyl-CoA is catalysed via β-ketothiolase activity not reliant on cysteine residues for catalysis such as the CYS-HIS-CYS catalytic triad associated with, for example, polyhydroxybutyrate producing bacterial species.

In some embodiments, the condensation of acryloyl-CoA and acetyl-CoA to form 3-oxopent-4-enoyl-CoA is catalysed via β-ketothiolase activity, such as that encoded by HFX_6004 (bktBα) and HFX_6003 (bktBβ), associated with haloarchaea.

In some embodiments, the condensation of acryloyl-CoA and acetyl-CoA to form 3-oxopent-4-enoyl-CoA is catalysed via β-ketothiolase activity associated with a SER-HIS-HIS catalytic triad.

Enzymes Generating 1,3-butadiene from 3-oxopent-4-enoyl-CoA

In some embodiments, 1,3-butadiene can be synthesized by, for example, the enzymes and metabolic pathways shown in FIG. 4.

Cultivation Strategy

In some embodiments, 3-oxopent-4-enoyl-CoA is biosynthesized in a recombinant host using a fermentation strategy that can include anaerobic, micro-aerobic or aerobic cultivation of the recombinant host.

In some embodiments, a cell retention strategy using, for example, ceramic hollow fiber membranes is employed to achieve and maintain a high cell density during either fed-batch or continuous fermentation in the synthesis of 3-oxopent-4-enoyl-CoA as central precursor to butadiene.

In some embodiments, the principal carbon source fed to the fermentation in the synthesis of 3-oxopent-4-enoyl-CoA derives from biological or non-biological feedstocks.

In some embodiments, the biological feedstock is, includes, or derives from, monosaccharides, disaccharides, lignocellulose, hemicellulose, cellulose, lignin such as levulinic acid and furfural, lignin, triglycerides such as glycerol and fatty acids, agricultural waste or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida* and *Yarrowia lipolytica* (Lee et al., *Appl. Biochem. Biotechnol.*, 2012, 166, 1801-1813; Yang et al., *Biotechnology for Biofuels*, 2012, 5:13; Meijnen et al., *Appl. Microbiol. Biotechnol.*, 2011, 90, 885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, *Journal of Biotechnology*, 2011, 155, 2011, 293-298; Martin and Prather, *Journal of Biotechnology*, 2009, 139, 61-67).

The efficient catabolism of lignin-derived aromatic compounds such as benzoate analogues has been demonstrated in several microorganisms such as *Pseudomonas putida* and *Cupriavidus necator* (Bugg et al., *Current Opinion in Biotechnology*, 2011, 22, 394-400; Pérez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7), 2419-2428).

The efficient utilization of fermentable sugars such as monosaccharides and disaccharides derived from cellulosic, hemicellulosic, cane and beet molasses, cassava, corn and other argricultural sources has been demonstrated for several microorganism such as *Escherichia coli, Corynebacterium glutamicum* and *Lactobacillus delbrueckii* and *Lactococcus lactis* (see, e.g., Hermann et al, *Journal of Biotechnology*, 2003, 104, 155-172; Wee et al., *Food Technol. Biotechnol.*, 2006, 44(2), 163-172; Ohashi et al., *Journal of Bioscience and Bioengineering*, 1999, 87(5), 647-654).

The efficient utilization of furfural, derived from a variety of agricultural lignocellulosic sources, has been demonstrated for *Cupriavidus necator* (Li et al., *Biodegradation*, 2011, 22, 1215-1225).

In some embodiments, the non-biological feedstock can be, or can be derived from, natural gas, syngas, $CO_2/H_2$, methanol, ethanol, non-volatile residue (NVR) or a caustic wash waste stream from cyclohexane oxidation processes.

The efficient catabolism of methanol has been demonstrated for the methylotropic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Köpke et al., *Applied and Environmental Microbiology*, 2011, 77(15), 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1), 152-156).

In some embodiments, the host microorganism is a prokaryote. For example, the prokaryote can be from the genus *Escherichia* such as *Escherichia coli*; from the genus *Clostridia* such as *Clostridium ljungdahlii*, *Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens*, *Pseudomonas putida* or *Pseudomonas oleavorans*; from the genus *Delftia* such as *Delftia acidovorans*; from the genus *Bacillus* such as *Bacillus subtilis*; from the genus *Lactobacillus* such as *Lactobacillus delbrueckii*; or from the genus *Lactococcus* such as *Lactococcus lactis*; from the genus *Synechococcus* such as *Synechococcus elongatus*. Such prokaryotes also can be sources of genes to construct recombinant host cells described herein that are capable of producing butadiene.

In some embodiments, the prokaryotic host microorganism is an archaeon. For example, the archaeon can be from the genus *Methanocaldococcus* such as *Methanocalcococcus jannaschii*; from the genus *Haloferax* such as *Haloferax mediterranei*; from the genus *Metallosphera* such as *Metallosphera sedula*; from the genus *Methanobacterium* such as *Methanobacterium thermoautotrophicum*; or from the genus *Pyrococcus* such as *Pyrococcus abyssi*.

In some embodiments, the host microorganism is a eukaryote. Eukaryotes can be, for example, fungi (e.g., filamentous fungi or yeasts). For example, the eukaryote can be from the genus *Aspergillus* such as *Aspergillus niger*; from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing butadiene.

Metabolic Engineering

The present document provides methods involving less than all the steps described for all the above pathways. Such methods can involve, for example, one, two, three, four, five, six, seven, eight, nine, ten, or more of such steps. Where less than all the steps are included in such a method, the first step can be any one of the steps listed. Again, all these methods can be in vitro (see above) or in recombinant host cells.

Furthermore, recombinant hosts described herein can include any combination of the above enzymes such that one or more of the steps, e.g., one, two, three, four, five, six, seven, eight, nine, ten, or more of such steps, can be performed within a recombinant host.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined in section 4.1 and section 4.2 are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined in section 4.1 and section 4.2 are gene dosed, i.e., overexpressed, into the resulting genetically modified organism via episomal or chromosomal integration approaches.

In some embodiments, genome-scale system biology techniques such as Flux Balance Analysis are utilized to devise genome scale attenuation or knockout strategies for directing carbon flux to butadiene.

Attenuation strategies include, but are not limited to; the use of transposons, homologous recombination (double cross-over approach), mutagenesis, enzyme inhibitors and RNAi interference.

In some embodiments, fluxomic, metabolomic and transcriptomal data are utilized to inform or support genome-scale system biology techniques, thereby devising genome scale attenuation or knockout strategies in directing carbon flux to butadiene.

In some embodiments requiring intracellular availability of propanoyl-CoA or acryloyl-CoA for 3-oxopent-4-enoyl-CoA synthesis, genes (e.g., endogenous genes) encoding enzymes catalyzing the hydrolysis of propionyl-CoA and acetyl-CoA can be attenuated in the host organism.

In some embodiments requiring the intracellular availability of propanoyl-CoA or acryloyl-CoA for 3-oxopent-4-enoyl-CoA synthesis, genes (e.g., endogenous genes) encoding enzymes consuming propanoyl-CoA via the methyl-citrate cycle can be attenuated in the host organism (Upton and Mckinney, *Microbiology*, 2007, 153, 3973-3982).

In some embodiments requiring the intracellular availability of propanoyl-CoA or acryloyl-CoA for 3-oxopent-4-enoyl-CoA synthesis, genes (e.g., endogenous genes) encoding enzymes consuming propanoyl-CoA to pyruvate can be attenuated in the host organism.

In some embodiments requiring the intracellular availability of propanoyl-CoA or acryloyl-CoA for 3-oxopent-4-enoyl-CoA synthesis, genes (e.g., endogenous genes) encoding enzymes consuming propanoyl-CoA to malonyl-CoA can be attenuated in the host organism.

In some embodiments requiring the intracellular availability of propanoyl-CoA or acryloyl-CoA via L-threonine as central metabolite for 3-oxopent-4-enoyl-CoA synthesis, a feedback-resistant threonine deaminase is genetically engineered into the host organism (Tseng et al., *Microbial Cell Factories*, 2010, 9:96).

In some embodiments requiring condensation of acetyl-CoA and acryloyl-CoA for 3-oxopent-4-enoyl-CoA synthesis, the genes (e.g., endogenous genes) encoding β-ketothiolases catalyzing the condensation of acetyl-CoA to acetoacetyl-CoA (such as the AtoB or phaA genes) can be attenuated.

In some embodiments using hosts that naturally accumulate polyhydroxyalkanoates, the genes (e.g., endogenous genes) encoding polymer synthase enzymes can be attenuated in the host strain.

In some embodiments requiring the intracellular availability of acetyl-CoA for 3-oxopent-4-enoyl-CoA synthesis, a host that is deficient (e.g., attenuated level of activity) in one or more enzymes in the acetate synthesis pathway can be used. For example, a host that is deficient in a phosphotransacetylase (encoded by the pta gene) can be used (Shen et al., *Appl. Environ. Microbio.*, 2011, 77(9), 2905-2915).

In some embodiments requiring the intracellular availability of acetyl-CoA for 3-oxopent-4-enoyl-CoA synthesis, a gene (e.g., an endogenous gene) in an acetate synthesis pathway encoding an acetate kinase, such as ack, can be attenuated.

In some embodiments requiring the intracellular availability of acetyl-CoA for 3-oxopent-4-enoyl-CoA synthesis, a gene (e.g., an endogenous gene) encoding an enzyme catalyzing the degradation of pyruvate to lactate, such as ldhA, can be attenuated (Shen et al., *Appl. Environ. Microbio.*, 2011, 77(9), 2905-2915).

In some embodiments requiring the intracellular availability of acetyl-CoA for 3-oxopent-4-enoyl-CoA synthesis, a gene (an endogenous gene) encoding an enzyme catalyzing the degradation of phophoenolpyruvate to succinate, such as frdBC, can be attenuated (see, e.g., Shen et al., 2011, supra).

In some embodiments requiring the intracellular availability of acetyl-CoA for 3-oxopent-4-enoyl-CoA synthesis, a gene (e.g., an endogenous gene) encoding an enzyme catalyzing the degradation of acetyl-CoA to ethanol, such as adhE, can be attenuated (Shen et al., 2011, supra).

In some embodiments, where pathways require excess NADPH co-factor in the synthesis of 3-oxopent-4-enoyl-CoA, a puridine nucleotide transhydrogenase gene, such as UdhA, can be overexpressed in the host organisms (Brigham et al., *Advanced Biofuels and Bioproducts*, 2012, Chapter 39, 1065-1090).

In some embodiments, where pathways require excess NADPH co-factor in the synthesis of 3-oxopent-4-enoyl-CoA, a glyceraldehyde-3P-dehydrogenase gene such as GapN can be overexpressed in the host organisms (Brigham et al., 2012, supra).

In some embodiments, where pathways require excess NADPH co-factor in the synthesis of 3-oxopent-4-enoyl-CoA, a malic enzyme gene, such as maeA or maeB can be overexpressed in the host organisms (Brigham et al., 2012, supra).

In some embodiments, where pathways require excess NADPH co-factor in the synthesis of 3-oxopent-4-enoyl-CoA, a glucose-6-phosphate dehydrogenase gene such as zwf can be overexpressed in the host organisms (Lim et al., *Journal of Bioscience and Bioengineering*, 2002, 93(6), 543-549).

In some embodiments, where pathways require excess NADPH co-factor in the synthesis of 3-oxopent-4-enoyl-CoA, a fructose 1,6 diphosphatase gene such as fbp can be overexpressed in the host organisms (Becker et al., *Journal of Biotechnology*, 2007, 132, 99-109).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of 3-oxopent-4-enoyl-CoA synthesis, the method comprising condensing acryloyl-CoA and acetyl-CoA using a protein with β-ketothiolase activity, wherein said protein is a heterodimer
wherein one of the two polypeptides of the heterodimer comprises a full-length protein encoded by a *Haloferax mediterranei* HFX_6004 (bktBα) gene comprising SEQ ID NO: 1, a functional fragment of the protein of SEQ ID NO:1 with β-ketothiolase activity, or a functional variant of the full-length protein of SEQ ID NO:1 having at least 95% sequence identity with the polypeptide of SEQ ID NO: 1 and exhibiting β-ketothiolase activity; and the other polypeptide of the heterodimer comprises a full-length protein encoded by a HFX_6003 (bktBβ) gene comprising SEQ ID NO:2, a functional fragment of the protein of SEQ ID NO:2 with β-ketothiolase activity, or a functional variant of the full-length protein of SEQ ID NO:2 having at least 90% amino acid sequence identity with the polypeptide of SEQ ID NO: 2 and exhibiting β-ketothiolase activity.

2. The method of claim 1, wherein at least one subunit of the protein is a polypeptide, or is derived from a polypeptide, encoded by an archaeon gene.

3. The method of claim 2, wherein the archaeon gene is a haloarchaeon gene.

4. The method according to claim 1, wherein the protein comprises a SER-HIS-HIS catalytic triad associated with its catalytic mechanism.

5. The method according to claim 1, wherein the acryloyl-CoA is produced using a butyryl-CoA dehydrogenase (EC 1.3.8.1), a medium-chain acyl-CoA dehydrogenase (EC 1.3.8.7), a 2-methylacyl-CoA dehydrogenase (EC 1.3.99.12), lactoyl-CoA dehydratase (EC 4.2.1.54) or a 3-hydroxypropionyl-CoA dehydratase (EC 4.2.1.116).

6. The method according to claim 1, wherein the method comprises a fermentation step which requires culturing a host cell that produces the protein with β-ketothiolase activity.

7. The method according to claim 6, wherein the host cell is a prokaryote or a eukaryote.

8. The method according to claim 7, wherein the prokaryote is a bacterium of the genus *Escherichia, Clostridia, Corynebacteria, Cupriavidus, Pseudomonas, Bacillus* or *Rhodococcus*.

9. The method according to claim 7, wherein the eukaryote is a fungus of the genus *Aspergillus, Saccharomyces, Pichia, Yarrowia, Issatchenkia, Debaryomyces, Arxula* or *Kluyveromyces*.

10. The method according to claim 7, wherein the prokaryote is an archaeon of the genus *Methanocaldococcus, Haloferax, Metallosphera, Methanobacterium* or *Pyrococcus*.

11. The method according to claim 6, wherein the fermentation step comprises anaerobic, micro-aerobic or aerobic cell cultivation.

12. The method according to claim 6, wherein cell retention strategies using ceramic hollow fibre membranes are employed to achieve and maintain a high cell density during fermentation.

13. The method according to claim 6, wherein the principal carbon source used in the fermentation step derives from biological or non-biological feedstocks.

14. The method according to claim 13, where the biological feedstock is, or derives from, monosaccharides, disaccharides, hemicellulose, cellulose, lignocellulose, lignin, triglycerides, agricultural waste or municipal waste.

15. The method according to claim 13, where the non-biological feedstock is, or derives from, natural gas, syngas, $CO_2/H_2$, methanol, ethanol, non-volatile residue (NVR), caustic wash from a cyclohexane oxidation processes, or a waste stream from the chemical or petrochemical industries.

* * * * *

SEQUENCE LISTING

```
<160> NUMBER OF SEQ ID NOS: 2

<210> SEQ ID NO 1
<211> LENGTH: 383
<212> TYPE: PRT
<213> ORGANISM: Haloferax mediterranei

<400> SEQUENCE: 1

Met Glu Val Ala Val Ile Gly Ser Ser Met Thr Lys Phe Gly Gln Arg
1               5                   10                  15

Ser Ala Trp Ile Arg Glu Leu Leu Ser Glu Ala Gly Gln Ala Cys Leu
            20                  25                  30

Glu Asp Ala Gly Val Ala Pro Ala Ser Val Asp His Leu Tyr Val Ser
        35                  40                  45

Asn Met Ala Ser Gly Glu Phe Glu Gly Gln Thr Gly Val Met Asn Ala
    50                  55                  60
```

Leu Ala His Asp Leu Gly Val Ile Pro Ala Tyr Thr Gln Arg Ile Asp
65                  70                  75                  80

Gln Thr Ser Ser Ser Gly Gly Ala Gly Ile Tyr Glu Ala Trp Gln Ser
                85                  90                  95

Ile Ala Ser Gly Val Ser Glu Met Thr Leu Val Gly Gly Glu Lys
            100                 105                 110

Met Thr His Lys Thr Thr Gly Glu Ser Thr Asp Ile Ile Ala Ser Cys
            115                 120                 125

Thr His Pro Glu Glu Tyr Lys His Gly Val Thr Leu Pro Ser Phe Ala
        130                 135                 140

Gly Met Thr Ala Arg Asn Tyr Leu Glu Arg Phe Asp Ala Pro Arg Glu
145                 150                 155                 160

Ser Leu Ala Arg Val Ala Val Lys Asn His Arg Asn Gly Val Asp Asn
                165                 170                 175

Pro Lys Ala Gln Phe Gln Lys Glu Ile Asp Ile Glu Thr Ala Leu Glu
            180                 185                 190

Ser Pro Ile Ile Ala Asp Pro Leu Arg Leu Tyr Asp Phe Cys Pro Ile
        195                 200                 205

Thr Asp Gly Ser Ala Ala Met Met Phe Thr Thr Glu Glu Arg Ala Gln
210                 215                 220

Glu Ile Thr Asp Glu Tyr Ala Ile Val Ser Gly Val Gly Gly Ala Thr
225                 230                 235                 240

Asp Thr His Val Val His Glu Arg Asp Pro Thr Val Met Gly Gly
                245                 250                 255

Val Val Glu Ser Ser Lys Gln Ala Tyr Glu Met Ala Gly Val Gly Pro
            260                 265                 270

Asp Asp Leu Asp Val Ala Glu Leu His Asp Met Phe Thr Ile Leu Glu
        275                 280                 285

Phe Leu Gln Leu Glu Gly Ile Gly Val Ala Asp His Gly Ala Ala Trp
        290                 295                 300

Glu Leu Ala Met Asp Gly Val Thr Ala Lys Asp Gly Gly Leu Pro Ile
305                 310                 315                 320

Asn Thr Ser Gly Gly Leu Lys Ser Lys Gly His Pro Leu Gly Ala Ser
                325                 330                 335

Gly Val Ala Gln Gly Val Glu Ile Tyr Glu Gln Leu Val Gly Glu Ala
            340                 345                 350

Gly Pro Arg Gln Val Glu Ala Asp Thr Ala Leu Ala Cys Asn Val Gly
        355                 360                 365

Gly Phe Gly Asn Cys Val Ile Thr Thr Ile Met Glu Ala Ala Lys
        370                 375                 380

<210> SEQ ID NO 2
<211> LENGTH: 61
<212> TYPE: PRT
<213> ORGANISM: Haloferax mediterranei

<400> SEQUENCE: 2

Met Ala Ile Val Glu Phe Glu Val Asp Gly Gln Ala Val Arg Ala Leu
1               5                   10                  15

Gly Gln Val Thr Thr Asp Asp Ile Glu Thr Gly Asp Val Val Glu Pro
            20                  25                  30

Val Tyr Val Glu Glu Leu Arg Asp Pro Glu Val Gly Ile Lys Ala Pro
        35                  40                  45

Glu Ser Gln Ser Trp Asp Gly Tyr Arg Trp Asp Pro Val
50                  55                  60